United States Patent
Fonte et al.

(10) Patent No.: US 9,045,515 B2
(45) Date of Patent: Jun. 2, 2015

(54) PROCEDURE FOR THE PURIFICATION OF TIACUMICIN B

(71) Applicant: OLON S.p.A., Rodano (IT)

(72) Inventors: Piera Fonte, Turin (IT); Giovanni Lazzari, Settimo Torinese (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 13/855,969

(22) Filed: Apr. 3, 2013

(65) Prior Publication Data

US 2013/0267692 A1 Oct. 10, 2013

(30) Foreign Application Priority Data

Apr. 5, 2012 (IT) .............................. MI2012A0560

(51) Int. Cl.
C07H 1/00 (2006.01)
C07H 1/08 (2006.01)
C07H 1/06 (2006.01)
C07H 17/08 (2006.01)

(52) U.S. Cl.
CPC .. *C07H 1/08* (2013.01); *C07H 1/06* (2013.01); *C07H 17/08* (2013.01)

(58) Field of Classification Search
CPC ............. C07H 1/06; C07H 1/08; C07H 17/08
USPC ......................................... 536/127
See application file for complete search history.

(56) References Cited

U.S. PATENT DOCUMENTS

| 3,978,211 A | 8/1976 | Coronelli et al. |
| 4,918,174 A | 4/1990 | McAlpine et al. |
| 7,507,564 B2 | 3/2009 | Shue et al. |

*Primary Examiner* — Elli Peselev
(74) *Attorney, Agent, or Firm* — Silvia Salvadori, P.C.

(57) ABSTRACT

The present invention relates to an improved process for the purification of tiacumicin B. Specifically, the invention relates to a simplified, optimised process for the purification of tiacumicin B from a fermentation broth, using chromatography techniques. In particular, the invention relates to a method for purifying tiacumicin B which comprises subjecting a liquid containing tiacumicin B to at least one hydrophobic interaction chromatography step.

The process according to the invention is simpler than the processes according to the prior art, and can easily be used on a large scale for commercial production.

10 Claims, No Drawings

PROCEDURE FOR THE PURIFICATION OF TIACUMICIN B

This application is a Non-Provisional Application which claims priority to and the benefit of Italian Application No. MI2012A000560 filed on Apr. 5, 2012, the content of which is incorporated herein by reference in its entirety.

FIELD OF INVENTION

The present invention relates to an improved process for the purification of tiacumicin B. Specifically, the invention relates to a simplified, optimised process for the purification of tiacumicin B from a fermentation broth, using chromatography techniques. The process according to the invention is simpler than the processes according to the prior art, and can easily be used on a large scale for commercial production.

PRIOR ART

Tiacumicin B belongs to the tiacumicin family; the tiacumicins, produced by fermentation of *Dactylosporangium aurantiacum*, are a group of 18-member unsaturated macrocycles belonging to the macrolide class, which differ by the type of substituents of the unsaturated ring. Tiacumicin B has the structure illustrated below:

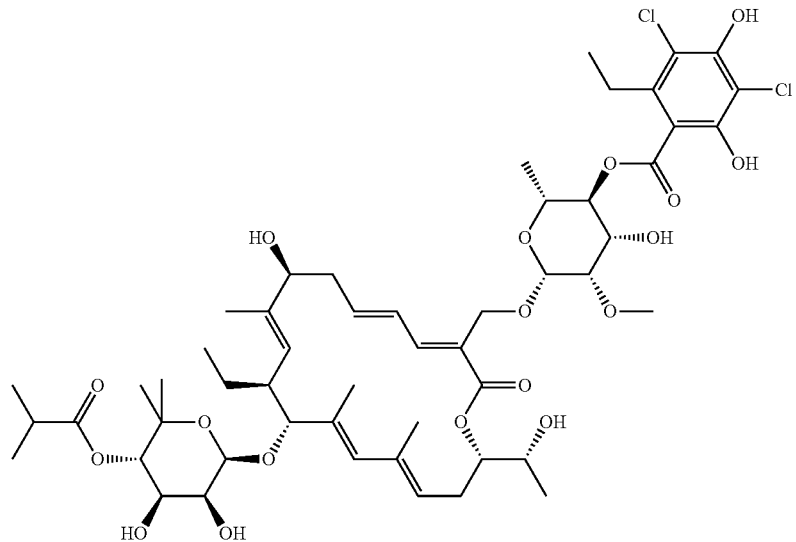 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](OC(=O)C(C)C)[C@H](O)[C@@H]3O)/C(C)=C/C(C)=C/C[C@@H]([C@@H](C)O)OC2=O)O[C@@H]1C]

The tiacumicins, in particular tiacumicin B, possess activity against numerous pathogenic bacteria, including *Clostridium difficile*.

Lipiarmycins are another product class closely related to tiacumicins. In particular, tiacumicin B is identical to lipiarmycin A3.

Lipiarmycin was isolated for the first time from *Actinoplanes deccanensis* in the 1970s. U.S. Pat. No. 3,978,211 claims lipiarmycin and a process for its production by fermenting *Actinoplanes deccanensis* ATCC 21983 in an aqueous nutrient medium containing assimilable sources of carbon, nitrogen and inorganic salts. The recovery of lipiarmycin, which is described (but not claimed) in the patent, uses conventional procedures, such as extraction of the broth with an organic solvent (butanol), purification of the crude product by chromatography (silica gel column; eluent: chloroform/methanol mixture), and finally, crystallisation from a mixture of diethyl ether and petroleum ether.

U.S. Pat. No. 4,918,174 claims tiacumicins and a process for their production by submerged aerobic fermentation of *Dactylosporangium aurantiacum* subspecies hamdenensis. The patent describes (but once again does not claim) the recovery of the antibiotics from the fermentation broth by extraction with an organic solvent, purification by solvent-solvent partitioning and chromatography (Sephadex LH-20 and silica gel).

U.S. Pat. No. 7,507,564 discloses an improved method for the production of tiacumicins. The patent claims the production of tiacumicins by culturing *Dactylosporangium aurantiacum* subspecies hamdenensis in a nutrient medium containing a certain quantity of adsorbent resin.

Said patent also discloses and claims a process of recovery of tiacumicin B from fermentation broth containing an adsorbent resin. The process described in said patent comprises: 1) extraction of the product from resin with a solvent or a solvent mixture; 2) precipitation of the crude product; 3) purification by chromatography (silica-gel chromatography, reverse-phase HPLC); and 4) crystallisation.

Consequently, to obtain the required results in terms of quality (purity >95%), a number of purification steps are required, including RP-HPLC, which penalises the process yield and makes it difficult to apply on a commercial scale.

There is therefore a need to develop a simple purification procedure, which can be performed on a large scale with a small number of steps to isolate purified tiacumicin B from a fermentation broth.

DESCRIPTION OF THE INVENTION

The present invention provides an improved process for the purification of tiacumicin B, resulting in a product with a purity of at least 95%. The method according to the invention uses Hydrophobic Interaction Chromatography (HIC). In addition to said step, normal isolation procedures can be performed, such as insolubilisation or crystallisation of the end product. The process described is simpler than those described in the prior art, and makes the use of RP-HPLC superfluous.

We have now found that when HIC columns with different pH values are used, different types of impurities can be eluted differentially, and therefore separated, which considerably improves the quality of the product. Said characteristic is unprecedented in this field, and could not be foreseen on the basis of the chemical properties and structure of the product. The method, which is described in greater detail below, provides a very simple purification process and a substantially pure product.

The present invention relates to a process for the recovery and purification of tiacumicin B which involves subjecting a liquid containing tiacumicin B to at least one hydrophobic interaction chromatography step.

Hydrophobic interaction chromatography uses a resin selected from the group of styrene-divinylbenzene absorbent resins. In particular, resins HP20, HP21, HP20SS, SP20, SP2OSS, SP825, SP850, SP207, XAD16, XAD1600, XAD18, etc., obtainable from Mitsubishi, Rohm & Haas, can be used. In a preferred form of embodiment, the resin is HP20SS with a very fine particle size.

The starting material of the process according to the present invention can be prepared by the method described in U.S. Pat. No. 4,918,174.

The fermentation broth used as starting material of the present invention is filtered and then purified by HIC. The filtered broth can be pre-purified before the chromatography step to eliminate compounds chemically different from tiacumicins and correlated substances with a significantly different polarity. Non-limiting steps of pre-treatment of the filtered broth include, for example, extraction with a water-immiscibile solvent or precipitation of the crude product.

Hydrophobic interaction chromatography preferably comprises the following steps:
a) loading the liquid containing tiacumicin B at a pH from 2.0 to 8.0, preferably from 2.5 to 6.5, onto the hydrophobic interaction resin;
b) eluting the impurities from the hydrophobic interaction resin with a mixture consisting of water and an organic solvent selected from methanol, ethanol, acetonitrile, acetone, THF or a mixture thereof with a pH from 2.0 to 8.0, preferably from 2.5 to 6.5;
c) eluting tiacumicin B from the hydrophobic interaction resin with a mixture consisting of water and an organic solvent selected from methanol, ethanol, acetonitrile, acetone, THF or a mixture thereof at a pH from 2.0 to 8.0, preferably from 2.5 to 6.5.

According to a preferred embodiment of the present invention, tiacumicin B is purified using two successive hydrophobic interaction chromatography steps.

During elution of the product, the fractions are isolated; the fractions containing the product of the desired purity are combined to give the eluate from the first HIC. This first step of HIC increases the purity of tiacumicin B from approx. 40% to 80% or more.

Next, after removal of the solvent, the solution of partly purified tiacumicin B is reloaded onto a column containing the same resin as the first hydrophobic interaction chromatography step, and undergoes a second hydrophobic interaction chromatography step. The solution is loaded onto the column at a pH in the 2.0 to 8 range; the pH of the solution is preferably in the 2.5 to 6.5 range. At the second step of HIC the resin, after loading, is washed with a suitable mixture consisting of water and an organic polar solvent under conditions wherein the impurities are dissociated from the resin, whereas the tiacumicin B remains bound to it. Finally, tiacumicin B is eluted under conditions wherein it is dissociated from the resin. The organic solvent is chosen from methanol, ethanol, acetonitrile, acetone, THF or mixtures thereof.

During elution of the product, the fractions are isolated; the fractions containing the product of the desired purity are combined to give the eluate from the second HIC step. This second step of HIC increases the purity of tiacumicin B from approx. 80% to 95% or more. Tiacumicin B is then isolated from the purified solution under standard conditions (i.e. by insolubilisation with an anti-solvent). The purified end product has a purity of at least 95%.

In a preferred form of embodiment of this invention, the two HIC columns are used at different pH values. This allows different types of compound to be separated on the basis of their differences of polarity, and the purity of the product to be improved. The order in which the two steps of HIC are conducted (at different pH values) is not crucial. According to one form of embodiment of the invention, the first step is conducted at pH 2.0-5.0, preferably 2.5-3.5, and the second step is conducted at pH 3.5-7.0, preferably 5-6.5.

EXAMPLE 1

The fermentation broth (10 l) containing tiacumicin B was extracted with 10 l of ethyl acetate. The ethyl acetate extract was concentrated to obtain 320 g of oily residue. The residue was dissolved in methanol at a concentration of 200 g/l. The resulting solution was loaded onto a column packed with HP20SS resin (1 l–50×5 cm) previously equilibrated with 5 bed volumes (BV) of phosphate buffer at pH 3.5. The column was washed with 10 BV of acetonitrile in phosphate buffer pH 3.5 (the % of acetonitrile ranges between 10% and 50%). The tiacumicin B was eluted with 5 BV of acetonitrile in acetate buffer pH 3.5 (the % of acetonitrile ranges between 52% and 60%). The eluate from the column was divided into fractions, and each fraction was analysed by HPLC to evaluate its purity. The fractions with a purity greater than 75% were combined and concentrated, and the concentrate was extracted with ethyl acetate. The ethyl acetate layer was concentrated to dryness, and the residue was redissolved in methanol at a concentration of 200 g/l. The resulting solution was loaded onto a column packed with HP20SS resin (0.2 l–40×2.5 cm) previously equilibrated with 5 BV of acetate buffer at pH 6.5. The column was washed with 10 BV of acetonitrile in acetate buffer pH 6.5 (the % of acetonitrile ranges between 10% and 45%). The tiacumicin B was eluted with 5 BV of acetonitrile in acetate buffer pH 6.5 (the % of acetonitrile ranges between 48% and 52%). The eluate from the column was divided into fractions, and each fraction was analysed by HPLC to evaluate its purity. The fractions with a purity greater than 95% were combined and concentrated, and the concentrate was extracted with ethyl acetate. The ethyl acetate layer was washed with 3 volumes of water and concentrated to a small volume, and 5 volumes of cyclohexane were added; the suspension was kept at 4° C. to complete the crystallisation. The product was filtered and dried. 0.45 g of white powder with a purity of 97.4% was obtained.

EXAMPLE 2

Crude tiacumicin B (16 g) was dissolved in methanol at a concentration of 200 g/l. The resulting solution was loaded onto a column packed with HP20SS resin (1 l–50×5 cm) previously equilibrated with 5 BV of acetate buffer at pH 5.0. The column was washed with 10 BV of acetonitrile in acetate buffer pH 5.0 (the % of acetonitrile ranges between 10% and 48%). The tiacumicin B was eluted with 5 BV of acetonitrile in acetate buffer pH 5.0 (the % of acetonitrile ranges between 50% and 55%). The eluate from the column was divided into fractions, and each fraction was analysed by HPLC to evaluate its purity. The fractions with a purity greater than 75% were combined and concentrated, and the concentrate was extracted with ethyl acetate. The ethyl acetate layer was concentrated to dryness, and the residue was redissolved in methanol at a concentration of 200 g/l. The resulting solution was loaded onto a column packed with HP20SS resin (1 1–50×5 cm) previously equilibrated with 5 bed volumes (BV) of phosphate buffer at pH 3.0. The column was washed with 10 BV of acetonitrile in phosphate buffer at pH 3.0 (the % of acetonitrile ranges between 10% and 52%). The tiacumicin B was eluted with 5 BV of acetonitrile in phosphate buffer at pH 3.0 (the % of acetonitrile ranges between 55% and 60%). The eluate from the column was divided into fractions, and each fraction was analysed by HPLC to evaluate its purity. The fractions with a purity greater than 95% were combined and concentrated, and the concentrate was extracted with ethyl acetate. The ethyl acetate layer was washed with 3 volumes of water and concentrated to a small volume, and 5 volumes of cyclohexane were added; the suspension was kept at 4° C. to complete the crystallisation. The product was filtered and dried. 2.8 g of white powder with a purity of 96.8% was obtained.

The invention claimed is:

1. A process for purifying tiacumicin B comprising subjecting a liquid containing tiacumicin B to at least one hydrophobic interaction chromatography step, wherein the hydrophobic interaction chromatographic step comprises:
    a) loading the liquid containing tiacumicin B at a pH ranging from 2.0 to 8.0 onto a hydrophobic interaction resin;
    b) eluting the impurities from the hydrophobic interaction resin with a mixture consisting of water and 10-52% acetonitrile at a pH at which the impurities are dissociated from the resin;
    c) eluting tiacumicin B from the hydrophobic interaction resin with a mixture of water and 48-60% acetonitrile at a pH at which the impurities are dissociated from the resin
    thereby obtaining purified tiacumicin B, wherein the liquid containing tiacumicin B is loaded twice onto the hydrophobic interaction resin, and wherein one hydrophobic interaction chromatography step uses, in elution steps b) and c), an eluent mixture having pH ranging from 2.0 to 5.0 and a subsequent hydrophobic interaction chromatography step uses, in elution steps b) and c), an eluent mixture having a pH range from 3.5 to 7.0, wherein the two chromatography steps are performed in any order.

2. The process according to claim 1 wherein the hydrophobic interaction chromatography uses a styrene-divinylbenzene resin.

3. The process according to claim 2 wherein the hydrophobic interaction chromatography uses a styrene-divinylbenzene resin selected from the group consisting of HP20, HP21, HP20SS, SP20, SP20SS, SP825, SP850, SP207, XAD16, XAD 1600 and XAD18.

4. The process according to claim 3 wherein the resin is HP20SS.

5. The process according to claim 1 wherein the liquid containing tiacumicin B is loaded at a pH ranging from 2.5 to 6.5 onto the hydrophobic interaction resin.

6. The process according to claim 1 wherein the pH of the eluent mixture used in elution step b) and/or c) is from 3.5 to 6.5.

7. The process according to claim 1 wherein one hydrophobic interaction chromatography step uses, in elution steps b) and c), an eluent mixture having a pH ranging from 2.5 to 3.5 and the subsequent hydrophobic interaction chromatography step uses, in elution steps b) and c), an eluent mixture having a pH ranging from 5.0 to 6.5, wherein the two chromatography steps are performed in any order.

8. The process according to claim 1 wherein the liquid containing tiacumicin B is a fermentation broth containing tiacumicin B.

9. The process according to claim 8 wherein the fermentation broth is subjected to filtration and optionally to pre-purification before the hydrophobic interaction chromatography step.

10. A process for purifying tiacumicin B comprising subjecting interacting at least once a liquid containing tiacumicin B to at least one hydrophobic interaction chromatography step, wherein the hydrophobic interaction chromatographic step comprises:
    a) loading the liquid containing tiacumicin B at a pH 3 onto a hydrophobic interaction resin;
    b) eluting the impurities from the hydrophobic interaction resin with a mixture consisting of water and 10-52% acetonitrile at a pH 3 at which the impurities are dissociated from the resin;
    c) eluting tiacumicin B from the hydrophobic interaction resin with a mixture of water and 55-60% acetonitrile at a pH 3 at which the impurities are dissociated from the resin with a resin suitable for hydrophobic interaction chromatography step; and
    thereby obtaining purified tiacumicin B.

* * * * *